United States Patent [19]

Ramelot

[11] 4,442,699
[45] Apr. 17, 1984

[54] MONITORING THE DUST CONTENT OF GASEOUS FLUID

[75] Inventor: Daniel Ramelot, St-Nicolas, Belgium

[73] Assignee: Centre de Recherches Metallurgiques-Centrum Voor Research in de Metallurgie, Brussels, Belgium

[21] Appl. No.: 236,973

[22] Filed: Feb. 23, 1981

[30] Foreign Application Priority Data

Feb. 25, 1980 [BE] Belgium ................................ 881910
Apr. 3, 1980 [BE] Belgium ................................ 882639

[51] Int. Cl.³ ............................................ G01N 31/00
[52] U.S. Cl. ............................................ 73/28
[58] Field of Search ................... 73/28, 863.12, 863.22, 73/863.23, 863.24, 863.25, 863.31, 863.41, 863.61, 863.81; 55/270

[56] References Cited

U.S. PATENT DOCUMENTS

| | | | |
|---|---|---|---|
| 3,377,867 | 4/1968 | Nitescu | 73/863.61 |
| 3,495,463 | 2/1970 | Howell | 73/863.12 |
| 3,841,145 | 10/1974 | Boubel | 73/28 |
| 4,034,611 | 7/1977 | Horling | 73/863.12 |
| 4,117,713 | 10/1978 | Phillips et al. | 73/28 |
| 4,140,006 | 2/1979 | d'Auzac et al. | 73/28 |
| 4,154,088 | 5/1979 | Werner | 73/28 |

FOREIGN PATENT DOCUMENTS 441469  10/1975  U.S.S.R. ............................... 73/28

Primary Examiner—Stephen A. Kreitman
Attorney, Agent, or Firm—Holman & Stern

[57] ABSTRACT

A continuously-taken sample of a dust-laden gaseous fluid is continuously passed through a filter for a given sampling period, this step being repeated at intervals. During each interval, while no fluid is passing through the filter, the filter is weighed after a hot dust-free gas has been passed through in order to dry the deposited dust. From the successive weights obtained, the weight of dust deposited during each sampling period is calculated.

9 Claims, 3 Drawing Figures

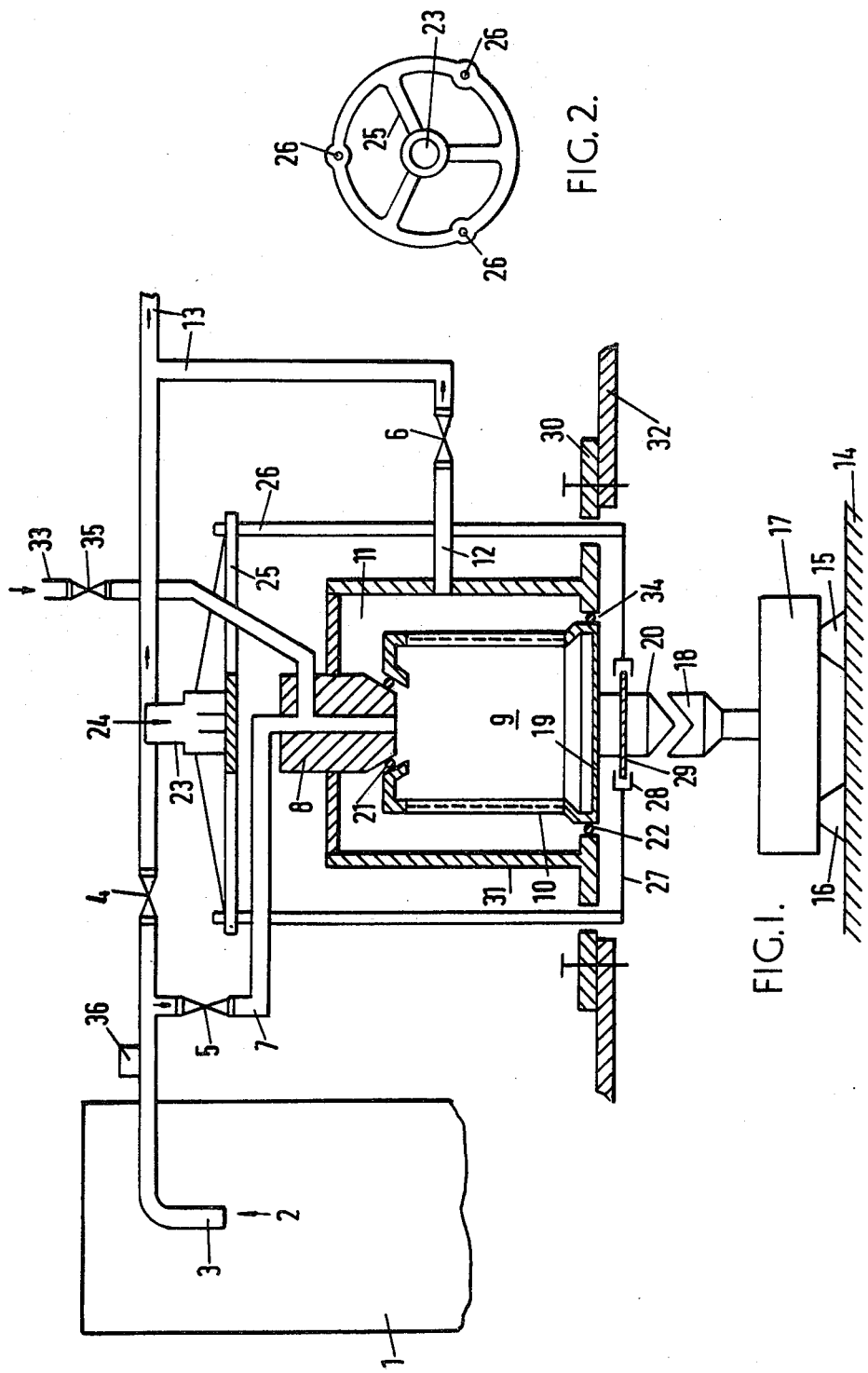

MONITORING THE DUST CONTENT OF GASEOUS FLUID

FIELD OF THE INVENTION

The present invention relates to improvements in methods and apparatus for monitoring the dust content of gaseous fluids. It may be applied in a particularly advantageous manner to the vapor produced during operations such as the production of agglomerates, cast iron, steel, non-ferrous metals, and powder material such as cement, etc.

DESCRIPTION OF THE PRIOR ART

In the majority of metallurgical operations in which vapor is produced, the overall dust content of this vapor, as well as its content of any solid or gaseous constituent, is in relation to the development of the operation and may, if it is measured, provide the operator with information concerning this development, enabling the operator to monitor it in an improved way.

The most commonly used method at present for determining the dust content of vapor moving in a given conduit includes taking a sample of the vapor from the conduit using isokinetic methods over a certain time period, this sample then being subjected to a filtering operation followed by drying of the dust and finally by weighing in a laboratory.

This method is disadvantageous as it is slow and only enables 5 to 6 measurements to be carried out per day, and also requires costly handling operations to be carried out in situ in an industrial plant. In addition, it is completely discontinuous and the results are only obtained after a minimum period of 24 hours, which does not enable effective action in terms of the monitoring of the process.

There are two main industrial methods for continuously evaluating the amount of dust:

(1) Measurement of the soiling of a filter by the absorption of radioactive radiation. However, this method is also discontinuous and is affected in addition by the nature of the dust collected by the filter (chemical composition, grain size, etc.).

(2) Measurement by optical methods of the attenuation of a ray (in the visible spectrum, or infrared) by the vapor passing between a radiation transmitter and receiver. This method has a considerable drawback in that it is not qualitative (the attenuation is dependent on the cross-section of the particles and not their volume).

At present there is no method, as far as the Inventor knows, enabling satisfactory continuous measurement of the dust content (by weight) of industrial vapor.

BRIEF SUMMARY OF THE INVENTION

One object of the invention is, therefore, to provide a method of this type in which the dust content by weight is ascertained from a sample of the vapor, this method being substantially continuous and enabling the drawbacks mentioned above to be remedied. Another object is to provide apparatus for performing this method.

The invention provides a method in which a sample of the vapor whose dust content is to be ascertained is taken, preferably using isokinetic methods, the sampling operation being carried out in a continuous manner, the sample is caused to pass through a filter in a continuous manner for a predetermined period of time, repeated at intervals which are preferably regular, during these intervals the filter is weighed, by means of any force sensor (for example a spring balance, a mechanical balance, an electronic balance, etc.) having a suitable sensitivity and measurement range, whilst during this time the sampled vapor is either removed along a path which bypasses the filter or the sampling is itself discontinued, the above cycle then being restarted, for example until the filter is completely saturated, and the weight of dust relating to each sampling period is deduced from the values of the successive weighing operations on the filter as it becomes increasingly loaded.

If the rate of flow of the sampled gas, restored to normal conditions (0° C. and 760 mm Hg), is measured in a continuous manner, the integration of this measurement over each sampling period enables the dust content of the vapor, expressed in $g/Nm^3$, to be calculated. Continuous measurement of the moisture content of the gases at right angles to a depressor enables this content to be corrected so as to be expressed in $g/Nm^3$ of dry gas.

Preferably, between the time at which a sampling period is discontinued (or the filter supply is discontinued) and the time at which the weighing operation is started, a compressed neutral or inert dry gas containing no dust (for example $N_2$) and having a temperature greater than 100° C. (preferably between 150° C. and 200° C.) is passed through the filter for a short time in order to eliminate any moisture from the layer of dust adjacent to the filter, which enables, in practice without a loss of time, the various weighing operations to be carried out on dry material. In order to improve this operation, the body of the filter may also be brought for a short time to a similar temperature (preferably the same time and the same temperature).

The method of the invention, as described above, enables measurements of the dust content of specific vapor to be carried out in a substantially continuous manner (for example 24 hours per day and 7 days per week), with a 15 minute interval, for example, between each measurement. The achievement of this result is facilitated by using a filter which is both very closely packed (i.e. does not allow dust having a diameter greater than 1 $\mu$m to pass through) and having a large capacity (for example a filter which may be used without difficulty for a very long period of approximately one week) before it needs to be cleaned or replaced, although this replacement may be carried out in a simple and rapid manner.

The present invention also relates to apparatus for carrying out the above-described method. Before describing the characteristic features of this apparatus, an embodiment given by way of non-limiting example will be described.

BRIEF DESCRIPTION OF THE DRAWINGS

In the drawings, which are not to scale:

FIG. 1 is a schematic general view, partly in section, of apparatus for measuring the dust content of vapor produced in an industrial process;

FIG. 2 is a plan view of part of the apparatus; and

DESCRIPTION OF PREFERRED EMBODIMENTS

Figure 3:
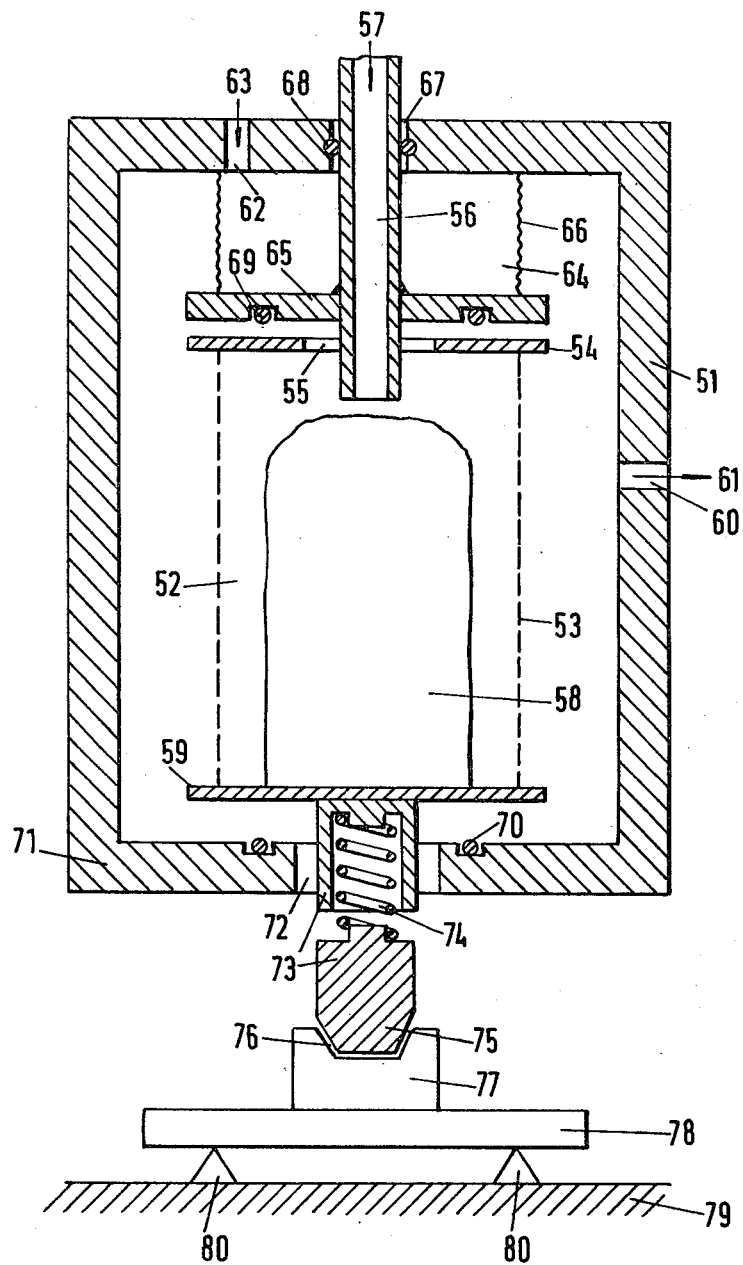
FIG. 3 shows a modified detail of the apparatus, in vertical section.

Vapor is displaced through a duct 1 in the direction of the arrow 2 (FIG. 1), a vapor sample being taken from the duct in an isokinetic manner by a pipe 3. During the sampling period, valve 4 is closed, whereas valves 5 and 6 are open. The vapor thus passes along the following path: valve 5, junction 7, connection 8, interior 9 of filter 10, permeable filter wall, chamber 11 surrounding filter, outlet 12, valve 6, evacuation duct 13.

In the interval during which weighing takes place, valves 5 and 6 are closed, whereas valve 4 is open, enabling the vapor to be discharge directly via duct 13.

The weighing device is constructed in the following manner. An electronic precision balance 17 is mounted on a base 14 by means of two damper blocks 15,16 and has its upper portion provided with a shaped connector 18 designed to support the mass to be weighed, in this case the filter 10 loaded with dust. The filter 10, which has its lower end 19 closed, is provided at this end with a shaft 20 whose end is shaped so as to fit the end of the connector 18. The filter 10 has two particular positions, i.e. an upper position in which it is subject to the action of the vapor (position shown in FIG. 1) and a lower position in which it rests its weight on the connector 18.

During the period in which the vapor passes through, the filter 10 is maintained in its upper position, in a leak-tight manner, in the chamber 11 by means of two O-rings 21 and 22. In this way, the vapor which enters through the connection 8 to the interior 9 of the filter may only be discharged through the filter wall.

As soon as the loading of the filter (sampling period) is complete, a jack 23 exerts a thrust in the direction of the arrow 24 on a frame 25 (see FIG. 2) connected by three rods 26 to a control disk 27 provided with an annular channel 28 which engages a circular collar 29 on the shaft 20 and causes the filter 10 to descend. During the displacement of the filter in the direction of the arrow 24, the filter ceases to contact the two O-rings 21,22 and rests with all its weight on the connector 18, by virtue of the play provided between the channel 28 and the collar 29. The casing 31 defining the chamber 11 is rigid with the connector 8 and with the outlet 12, supports the O-rings 21 and 22, and is fixed in a rigid manner to a chassis 32 by means of its base 30 provided with an aperture 34 in which the O-ring 22 is fixed.

As soon as the weighing phase is complete, the jack 23 rises in the opposite direction to the arrow 24 and the channel 28 raises the collar 29, which moves the filter 10 back into its upper position corresponding to the passage of vapor. It should be noted that, just after the end of the throughput period of the dust-laden gases, but before weighing has been started, a dry neutral dust-free gas at a suitable temperature (e.g. compressed nitrogen at 150°–200° C.) is blasted for a short time through a conduit 33, a valve 35, and the connector 8 into the filter 10, in such a way as to completely dry the dust collected by the filter. At this time the valves 35 and 6 are open, whilst the valves 4 and 5 are closed. From a technological point of view, the filter advantageously comprises a cylinder of a suitable porous paper, which cylinder is held in a metal grid having large mesh, so as to prevent any tearing of the paper. The vapor flow rate is measured by a meter 36.

In the modified detail illustrated in FIG. 3, the displacement of the filter is carried out in a particular manner. A casing 51 surrounds a filter 52 having a cylindrical permeable wall 53. At its input, the filter comprises a plate 54 with a central hole 55 through which passes the dust-laden gaseous fluid conveyed through a duct 56 in the direction of the arrow 57. After contacting the filter material 58 supported in the filter 52 on a base 59, the fluid escapes through the wall 53 and is discharged from the casing 51 via a port 60 in the direction of the arrow 61. In addition the casing 51 has an aperture 62 through which a compressed gas enters (in the direction of the arrow 63) which fills a closed auxiliary chamber 64 defined at the bottom by a base 65 and laterally by a leak-tight cylindrical wall 66, whose length may be varied, and at the top by the upper portion of the casing 51 surrounding a hole 67 through which the duct 56 passes, in a leak-tight manner by means of the O-ring 68. A second O-ring 69 rigid with the lower face of the base 65 surrounds the duct 56, whilst a third O-ring 70 rigid with the internal face of the base 71 of the casing 51 surrounds a circular aperture 72 provided in this base. The O-rings 69,70 are housed in trapezoidal grooves which prevent them from adhering to the filter 52 during the weighing phase described below.

The base 59 of the filter 52 has an external coaxial shaft 73 of compound construction, whose length may be varied under the effect of a spring 74. The lower portion 75 of this shaft is shaped so as to fit into a cavity 76 in a support 77 resting on an electronic balance 78 which is itself supported on a fixed seat 79 by means of two anti-vibrational bed plates 80.

During the blasting (sampling) period, the auxiliary chamber 64 is pressurized by the gas entering via the aperture 62, the base 65 is displaced downwardly until first the O-ring 69 comes into contact with the plate 54 and then until the filter 52, under the effect of the pressure still acting on the base 65, contacts with its base 59 the lower O-ring 70. The movement of the base 59 is made possible by the spring 74. At this moment, the hole 55 is closed in a leak-tight manner and the gaseous fluid is introduced into the filter 52 via the duct 56, in order to be discharged through the filter wall 53 after having given up its dust to the material 58.

As soon as the fluid supply is discontinued, the gas pressure in the chamber 64 is also discontinued and its base 65 rises releasing the filter 52, which, under the action of the spring 74, also rises. At this moment, the entire filter 52 is supported solely on the balance 78 (by means of the shaft 73) and the weighing operation may be carried out.

According to this embodiment, the device for making the filter leak-tight in the casing 51 is provided by means of two O-rings 69,70, one of which 69 is disposed between the upper plate 54 of the filter and the base 65 of the auxiliary chamber 64 serving to convey the gaseous fluid, and the other of which 70 is disposed between the base 59 closing the lower end of the filter and the base 71 of the casing 51 and which thus seals off the aperture 72 provided in the casing in order to provide a passage for extension 73 at this end of the filter. As a result of this arrangement, the sealing joints have a considerable advantage in that they are not subject to any torsional, bending, or shearing stresses, which ensures a long service life, even with high measuring rates. In addition, the arrangement illustrated makes them less sensitive to soiling by dust deposits.

Having described preferred embodiments of the apparatus, it is now possible to describe its characteristic features in general terms. The apparatus of the present invention comprises:

a dust filter, preferably having a cylindrical shape and a vertical axis, which filter has one end closed and the other end connected to a conduit designed to convey vapor to be filtered, a chamber which surrounds, in a leak-tight manner, the filter in a sampling position and which comprises a duct for the removal of the filtered vapor, means for displacing the filter from the sampling position to a weighing position, in which the filter is no longer disposed in a leak-tight manner in the chamber, but rests with its weight on a precision balance disposed below the filter, the said means enabling the filter to be returned to its normal sampling position, means for sampling, in a continuous manner, a sample of the vapor and for conveying this vapor to the input of the filter, a set of valves disposed on the conduits supplying the vapor for filtering and on the conduits for removing the vapor after filtration, means for measuring an instantaneous rate of flow of the gases sampled corresponding to each sampling period in order to calculate the amount of dust by weight in g/Nm$^3$.

According to an advantageous embodiment of this apparatus, it comprises in addition a device for supplying the filter with a dry neutral gas at a temperature greater than 100° C., and a device for heating (for example electrically) the filtering chamber.

Preferably, the precision balance is of the type which accumulates and stores data in a memory and is provided with vibration dampers.

It has also been found to be advantageous to fasten the end of the vapor inlet conduit into the wall of the chamber located on the input side of the filter, which simplifies the construction of the assembly, enables the vapor to enter the filter through its upper surface and substantially along its axis and consequently, forces the vapor to leave the chamber laterally, stripped of its dust.

Also, the device for making the filter leak-tight in the chamber is preferably provided by means of two O-rings, one of which is disposed between the filter input and the outlet end of the vapor inlet conduit or rigid with this end and the other of which is disposed between the closed end of the filter and a circular aperture provided in the chamber for the passage of this end of the filter or its extension. In addition, it has proved advantageous for the filter to be supported on the balance by means of its closed end.

The apparatus described above may be constructed in a plurality of ways and enables the measurement of the dust content of gaseous fluids of different types in a continuous manner with a high measuring rate (for example every fifteen minutes) and for a very long time (for example one week). This advantage is provided in particular by means of the use of a filter having a large capacity, which may have a very long service life before it needs to be replaced. A filter of this type may for example comprise a sheet of suitable porous paper or cellulose surrounded by a metallic lattice for protection against possible tearing.

In conclusion, the preferred apparatus is characterised by the use of a weighing device, of an extremely sensitive type, which is associated with electromechanical or electronic means which ensure a completely automatic and reproducible sequence of placing and lifting a filtering element on the weighing device, comprising:

sealing means between the body of the filter and the filtering element, during the vapor sampling phase, means for guiding the filter and for completely releasing it during the measuring phase in order to avoid any mechanical stress which could impair the accuracy of the measurement, mechanical, pneumatic, or electrical damping means, and timing means designed to prevent the measurement of transitory phenomena, electronic means for displaying the measurements and for calculating the characteristic values of the vapor, in particular the dust content of the vapor in g/Nm$^3$, means for selectively heating the conduits and the body of the filter and for the heat insulation of the weighing device in order to eliminate the water contained in the dust to be weighed.

I claim:

1. Apparatus for monitoring the dust content of a dust-laden gaseous fluid, comprising
   (a) a dust filter having an input side and an output side;
   (b) means for moving the filter between a sampling position and a weighing position;
   (c) a chamber which surrounds the filter in a leak-tight manner when the filter is in the sampling position, the chamber having an inlet conduit on the input side of the filter and an outlet conduit on the output side of the filter;
   (d) means for weighing the filter in the weighing position, the weight of the filter in the weighing position being wholly supported by the weighing means, the filter in the weighing position being no longer surrounded in a leak-tight manner by the chamber;
   (e) means for continuously taking a sample of the dust-laden gaseous fluid;
   (f) means for conveying the sample to the inlet conduit of the chamber to pass through the filter in the sampling position; and
   (g) means for preventing the sample from passing through the filter in the weighing position.

2. The apparatus of claim 1, including means for passing dust-free gas at a temperature of 100° C. through the filter.

3. The apparatus of claim 1, in which the weighing means comprises a precision balance having a data memory store.

4. The apparatus of claim 3, in which the balance has vibration dampers.

5. The apparatus of claim 1, in which the filter is of cylindrical shape, with a vertical axis, having a permeable cylindrical wall, a closed lower end, and an upper end with an inlet opening which communicates with the inlet conduit of the chamber when the filter is in the sampling position.

6. The apparatus of claim 5, in which the inlet conduit is directed along the vertical axis of the filter.

7. The apparatus of claim 5, in which the lower end of the filter extends through an aperture in a base portion of the chamber.

8. The apparatus of claim 7, further comprising means for sealing the said aperture and the inlet opening of the upper end of the filter when the filter is in the sampling position.

9. The apparatus of claim 1, further comprising means for measuring the instantaneous rate of flow of the continuously-taken sample.

* * * * *